(12) United States Patent
Buchanan et al.

(10) Patent No.: US 9,927,345 B2
(45) Date of Patent: Mar. 27, 2018

(54) NOZZLE ASSEMBLY FOR A FLOW CYTOMETER

(71) Applicant: Inguran, LLC, Navasota, TX (US)

(72) Inventors: Kris Buchanan, Fort Collins, CO (US);
Johnathan Charles Sharpe, Hamilton (NZ); Kenneth Michael Evans, College Station, TX (US)

(73) Assignee: Inguran, LLC, Navasota, TX (US)

( * ) Notice: Subject to any disclaimer, the term of this patent is extended or adjusted under 35 U.S.C. 154(b) by 19 days.

(21) Appl. No.: 15/204,838

(22) Filed: Jul. 7, 2016

(65) Prior Publication Data

US 2016/0320287 A1    Nov. 3, 2016

Related U.S. Application Data

(63) Continuation of application No. 13/831,332, filed on Mar. 14, 2013, now Pat. No. 9,404,846.

(60) Provisional application No. 61/703,102, filed on Sep. 19, 2012.

(51) Int. Cl.
  *B05B 1/08* (2006.01)
  *G01N 15/14* (2006.01)
  *G01N 33/487* (2006.01)

(52) U.S. Cl.
  CPC ..... *G01N 15/1404* (2013.01); *G01N 15/1434* (2013.01); *G01N 33/487* (2013.01); *G01N 2015/1409* (2013.01); *G01N 2015/149* (2013.01); *Y10T 29/49401* (2015.01)

(58) Field of Classification Search
  CPC ........... G01N 15/1404; G01N 15/1434; G01N 33/487; G01N 2015/1409; G01N 2015/149; Y01T 29/49401; B05B 5/03; B05B 1/08; B05B 7/045
  USPC ..................................... 239/290, 291, 102.1
  See application file for complete search history.

(56) References Cited

U.S. PATENT DOCUMENTS

| 3,672,324 | A | 6/1972 | Schnedler |
|---|---|---|---|
| 3,893,766 | A | 7/1975 | Hogg |
| 4,361,400 | A | 11/1982 | Gray et al. |
| 4,362,246 | A | 12/1982 | Adair |
| 4,660,971 | A | 4/1987 | Sage et al. |
| 4,737,025 | A | 4/1988 | Steen |
| 4,798,008 | A | 1/1989 | Belanger et al. |

(Continued)

FOREIGN PATENT DOCUMENTS

| CA | 2296324 A1 | 2/1999 |
|---|---|---|
| CA | 2739572 A1 | 11/2001 |

(Continued)

OTHER PUBLICATIONS

New Zealand Notice of Acceptance dated Sep. 7, 2016 in related NZ Appl. No. 706552.

(Continued)

*Primary Examiner* — Davis Hwu
(74) *Attorney, Agent, or Firm* — Ryan Christensen; Hashim Rahman

(57) ABSTRACT

A nozzle assembly is disclosed. The nozzle assembly may include a nozzle outlet and enclose a nozzle cavity. A sample inlet formed in the nozzle housing may provide fluid communication to an injection tube mounted in an injection stem formed in the nozzle housing. One or more sheath inlet may provide fluid communication with the nozzle cavity and a downstream exit orifice.

18 Claims, 6 Drawing Sheets

(56) References Cited

U.S. PATENT DOCUMENTS

| | | | |
|---|---|---|---|
| 4,813,609 | A | 3/1989 | French |
| 4,848,670 | A | 7/1989 | Belanger et al. |
| 4,988,619 | A | 1/1991 | Pinkel |
| 5,088,816 | A | 2/1992 | Tomioka et al. |
| 5,135,759 | A | 8/1992 | Johnson |
| 5,311,290 | A | 5/1994 | Olson et al. |
| 5,371,585 | A | 12/1994 | Morgan et al. |
| 5,439,362 | A | 8/1995 | Spaulding |
| 5,466,572 | A | 11/1995 | Sasaki et al. |
| 5,483,469 | A | 1/1996 | Van den Engh et al. |
| 5,601,234 | A | 2/1997 | Larue |
| 5,602,039 | A | 2/1997 | Van den Engh |
| 5,602,349 | A | 2/1997 | Van den Engh |
| 5,660,997 | A | 8/1997 | Spaulding |
| 5,690,895 | A | 11/1997 | Matsumoto et al. |
| 5,700,692 | A | 12/1997 | Sweet |
| 5,726,364 | A | 3/1998 | Van den Engh |
| 5,985,216 | A | 11/1999 | Rens |
| 6,089,078 | A | 7/2000 | Chelveder |
| 6,133,044 | A | 10/2000 | Van den Engh |
| 6,149,867 | A | 11/2000 | Seidel |
| 6,248,590 | B1 | 6/2001 | Malachowski |
| 6,267,301 | B1 | 6/2001 | Haruch |
| 6,263,745 | B1 | 7/2001 | Buchanan |
| 6,357,307 | B2 | 3/2002 | Buchanan |
| 6,491,190 | B1 | 12/2002 | Dunworth |
| 6,604,435 | B2 | 8/2003 | Buchanan |
| 6,746,873 | B1 | 6/2004 | Buchanan |
| 6,782,768 | B2 | 8/2004 | Buchanan |
| 7,012,689 | B2 | 3/2006 | Sharpe |
| 7,024,316 | B1 | 4/2006 | Ellison et al. |
| 7,780,095 | B2 | 8/2010 | Babaev |
| 7,855,078 | B2 | 12/2010 | Evans |
| 7,913,938 | B2 * | 3/2011 | Cooper .............. B05B 5/03 239/291 |
| 7,923,252 | B2 | 4/2011 | Van den Engh |
| 8,043,553 | B1 | 10/2011 | Durcan |
| 2002/0084290 | A1 | 7/2002 | Materna |
| 2003/0042326 | A1 | 3/2003 | Jameson et al. |
| 2004/0053243 | A1 | 3/2004 | Evans et al. |
| 2004/0169876 | A1 | 9/2004 | Sharpe et al. |
| 2005/0112541 | A1 | 5/2005 | Durack et al. |
| 2005/0180885 | A1 | 8/2005 | Tateishi |
| 2006/0141628 | A1 | 6/2006 | Evans |
| 2006/0263829 | A1 | 11/2006 | Evans et al. |
| 2007/0269348 | A1 | 11/2007 | Van den Engh et al. |
| 2008/0113447 | A1 | 5/2008 | Krager et al. |
| 2008/0230632 | A1 | 9/2008 | Fenton et al. |
| 2010/0009333 | A1 | 1/2010 | Auer |
| 2011/0010144 | A1 | 1/2011 | Fox et al. |
| 2011/0076712 | A1 | 3/2011 | Gilligan |
| 2011/0259749 | A1 | 10/2011 | Kanda |
| 2012/0200857 | A1 | 8/2012 | Sharpe et al. |

FOREIGN PATENT DOCUMENTS

| | | |
|---|---|---|
| CN | 103013811 A | 4/2013 |
| EP | 0288029 A2 | 4/1988 |
| EP | 1716798 A2 | 11/2006 |
| JP | 62117554 U | 7/1987 |
| JP | H02 118852 | 9/1990 |
| JP | H05 034262 A | 2/1993 |
| JP | 2004205217 A | 7/2004 |
| JP | 2012137507 A | 7/2012 |
| WO | 96/12171 | 4/1996 |
| WO | 99/05504 | 7/1998 |
| WO | 01/40765 | 7/2001 |
| WO | 2013192495 A2 | 12/2013 |

OTHER PUBLICATIONS

Chinese Notice of Decision for Granting Patent Right dated Sep. 12, 2016 in related CN Appl. No. 201380048073.1.
Australian Patent Examination Report dated Aug. 15, 2016 in related AU 20133318621.
New Zealand Examination Report dated Aug. 1, 2016 in related NZ Appl. No. 722143.
New Zealand Notice of Acceptance dated Aug. 1, 2016 in related NZ Appl. No. 630373.
Japanese Notice of Final Rejection dated Jul. 7, 2016 in related JP Appl. No. 2015-531910.
Japanese Notice of Final Rejection dated Jul. 7, 2016 in related JP Appl. No. 2015-532183.
Chinese Notification of Office Action dated Aug. 18, 2016 in related CN Appl. No. 201380048020.X.
European Search Report dated May 31, 2016 for related EP 13839833.4.
Canadian Examination Report dated Dec. 14, 2016 for related 2,885,170.
Japanese Notice of Final Rejection dated Nov. 9, 2016 in related JP Appl. No. 2015-532183.
U.S. Office Action dated Oct. 12, 2016 in related U.S. Appl. No. 14/426,451.
Australian Notice of Acceptance dated Feb. 8, 2017 in related AU 20133318621.
Chinese Notification of Office Action dated Mar. 16, 2017 in related CN Appl. No. 201380048020.X.
Chinese Office Action dated Mar. 16, 2016 issued in related CN Appl. No. 201380048073.1.
New Zealand Examination Report dated Apr. 13, 2016 issued in related 706552.
New Zealand Examination Report dated Apr. 14, 2016 issued in related 630368.
New Zealand Examination Report dated Apr. 13, 2016 issued in related 630373.
European Search Report dated Apr. 15, 2016 in related EP Application. 13838116.5.
Australian Patent Examination Report dated Jan. 19, 2016 for related AU application No. 2013318001.
NZ Notice of Acceptance dated Dec. 22, 2015 issued in related in NZ application 2013202631.
Chinese Office action dated Dec. 2, 2015 issued in related CN application No. 201380048020.X.
U.S. Office Action dated Dec. 14, 2015 issued in related U.S. Appl. No. 14/426,451.
Japanese Reasons for Rejection dated Feb. 23, 2016 for JP Application No. 2015-532183.
Japanese Reasons for Rejection dated Feb. 25, 2016 for JP Application No. 2015-531910.
New Zealand Office Action dated Apr. 22, 2015 in related NZ Patent Application No. 630373.
New Zealand Office Action dated Apr. 22, 2015 in related NZ Patent Application No. 706552.
New Zealand Office Action dated Jun. 15, 2015 in related NZ Patent Application No. 630368.
U.S. Office Action dated Jun. 23, 2015 in related U.S. Appl. No. 14/032,086.
U.S. Notice of Allowance dated Mar. 2, 2015 issued in corresponding U.S. Appl. No. 13/831,254.
U.S. Office Action dated Mar. 10, 2015 issued in corresponding U.S. Appl. No. 14/032,086.
AU Examination Report dated Apr. 13, 2015 issued in corresponding AU Application No. 2013202631.
U.S. Office Action dated Nov. 18, 2014 for Related U.S. Appl. No. 13/831,254.
Australian Notice of Acceptance dated Jul. 24, 2014, issued in related AU Application No. 2013202615.
Australian Examination Report dated Dec. 18, 2013, in related AU Application No. 2013202615.
PCT International Search Report and Written Opinion dated Feb. 2, 2014, issued in related PCT Application No. PCT/US 2013/60730.
International Search Report dated Jul. 22, 2013 in related International Patent Application No. PCT/US2013/031787.
Dean, P.N., et al., "Hydrodynamic orientation of spermatozoa heads for flow cytometry", Biophys. J. 23: 7-13, 1978.

(56) References Cited

OTHER PUBLICATIONS

Fulwyler, M.J., "Hydrodynamic orientation of cells." J Histochem. Cytochem, 1977, 25:781-783.
Gumsey, M.P., and Johnson, L.A., "Recent improvements in efficiency of flow cytometric sorting of X and Y chromosome bearing sperm of domestic animals: a review", 1998, New Zealand Society of Animal Protection.
Johnson, L.A., et al., "Enhanced flow cytometic sorting of mammalian X and Y sperm: high speed sorting and orienting for artificial insemination", Theriogenology. 49 (1): 361. abstr, 1998.
Johnson, L.A., et al., "Flow cytometry of X- and Y-chromosome bearing sperm for DNA using an improved preparation method and staining with Hoechst 333-42", Gamete Research 17: 203-212, 1987.
Johnson L.A., et al., "Modification of a laser-based flow cytometer or high resolution DNA analysis of mammalian spermatozoa" Cytometry 7:266-273, 1986.
Johnson LA, et al., "Improved flow sorting resolution of X- and Y-chromosome bearing viable sperm separation using dual staining and dead cell gating", Cytometry 17 (suppl 7): 83, 1994.
Johnson, LA., et al., "Sex Preselection: High Speed Flow Cytometric Sorting of X and Y sperm for Maximum Efficiency" Theriogenology 52: 1323-1341, 1999.
Johnson, L.A., et al., "Sex preselection in rabbits: Live births from X and Y sperm separated by DNA and cell sorting" Bio Reprod 41: 199-203, 1989.
Kachel, V., et al., "Uniform Lateral Orientation, Caused by Flow Forces, of Flat Particles in Flow-Through Systems", The Journal of Histochemistry and Cytochemistry, 1997, vol. 25, No. 7, pp. 774-780.
Rens, W., et al., "Improved Flow Cytometric Sorting of X- and Y-Chromosome Bearing Sperm: Substantial Increase in Yield of Sexed Semen", Molecular Reproduction and Development, 1999, pp. 50-56.
Rens, W., et al., "A Novel Nozzle for More Efficient Sperm Orientation to Improve Sorting Efficiency of X and Y Chromosome-Bearing Sperm", Technical Notes, Cytometry 33, 1998, pp. 476-481.
Siedel, G.E. Jr., et al., "Artificial insemination of heifers with cooled, unfrozen, and sexed semen." Theriogenoloy, 1998, 49 (1): 365.
Welch G.R., et al., "Fluidic and optical modifications to a ACS IV for flow sorting of X- and Y-chromosome bearing sperm based on DNA", Cytometry 17 (suppl. 7): 74, 1994.
U.S. Notice of Allowance dated Jun. 22, 2016 issued in corresponding U.S. Appl. No. 13/831,332.
U.S. Notice of Allowance dated Feb. 9, 2016 issued in corresponding U.S. Appl. No. 13/831,332.
U.S. Office Action dated Oct. 9, 2015 for Related U.S. Appl. No. 13/831,332.
U.S. Office Action dated Feb. 3, 2015 for Related U.S. Appl. No. 13/831,332.
U.S. Office Action dated May 21, 2015 for Related U.S. Appl. No. 13/831,332.
Australian Notice of Acceptance dated Jun. 6, 2016 for related AU application No. 2013318001.
Canadian Examiner's Requisition dated Apr. 3, 2017 issued in related CA Appl. No. 2,885,234.
U.S. Office Action dated May 15, 2017 issued in related U.S. Appl. No. 14/426,451.
New Zealand Examination Report dated Oct. 20, 2017 issued in related NZ Appl. No. 722143.
Japanese Office Action dated Sep. 28, 2017 in related JP application No. 2015-15402.
Chinese Office Action dated Sep. 30, 2017 issued in related CN Appl. No. 722143.
Canadian Office Action dated Sep. 20, 2017 in related CA application No. 2,885,170.
Japanese Office Action dated Oct. 30, 2017 in related JP application No. 2016-202250.
Japanese Office Action dated Jan. 15, 2018 issued in related JP application No. 2015-531910.
U.S. Office Action dated Feb. 7, 2018 issued in related U.S. Appl. No. 14/426,451.

\* cited by examiner

NOZZLE ASSEMBLY FOR A FLOW CYTOMETER

This Application is Continuation of U.S. patent application Ser. No. 13/831,332, filed on Mar. 14, 2013, which claims the benefit of U.S. Provisional Application No. 61/703,102, filed on Sep. 19, 2012, the entire contents of which are incorporated herein by reference.

FIELD OF THE INVENTION

The present invention generally relates to the field of flow cytometry and more particularly to a nozzle assemblies for a flow cytometer systems and methods of manufacturing the same.

BACKGROUND

Flow cytometers have been known for analyzing and sorting particles, and are particularly suited to measure physical and chemical properties of biological materials, such as cells. In operation, a flow cytometer produces a fluid stream which includes a sample fluid containing particles of interest. These particles may be individually inspected in the fluid stream with a variety of sensing systems or detection devices and classified.

Sorters may additionally provide a mechanism for isolating subpopulations of particles based on their measured or determined properties. Jet-in-air flow cytometers achieve this separation through the creation and isolation of charged droplets containing particles of interest. The particle-containing droplets may be formed from the fluid stream and charged based upon a sort decision and, as they pass through an electrical field produced by deflection plates, their path is redirected into one of several predetermined trajectories for collection. The formation of these droplets may be achieved at a flow cytometer nozzle.

In addition to the function of droplet formation, a flow cytometer nozzle may aide in biasing particles toward a uniform orientation. This function enables the analysis and sorting of cells which have aspherical properties. In particular, the speeds at which sperm can be sorted into gender enriched populations have been increased, in part, due to the development of an orienting nozzle which presents a larger portion of the sperm in a relatively uniform orientation.

SUMMARY OF THE INVENTION

Certain embodiments of the claimed invention are summarized below. These embodiments are not intended to limit the scope of the claimed invention, but rather serve as brief descriptions of possible forms of the invention. The invention may encompass a variety of forms which differ from these summaries.

One embodiment relates to a method of manufacturing a nozzle assembly. Such a method may begin with the step of obtaining one or more nozzle components and continue with molding one or more nozzle housing pieces, such that at least one nozzle housing piece is over molded onto at least one of the nozzle components. Finally the nozzle housing pieces and nozzle components may be assembled into a nozzle assembly.

One embodiment provides for a nozzle assembly constructed from a nozzle housing which encloses a nozzle cavity. A sample inlet may be formed in the nozzle housing and connected to an injection tube having a sample outlet. The injection tube can be mounted to extend along the nozzle cavity and may include a flow path providing fluid communication between the sample inlet and a sample outlet. A nozzle exit orifice may be located downstream of the sample outlet and one or more sheath inlets may be in fluid communication with the nozzle cavity.

Another embodiment provides a flow cytometer system that can include a sample source supplying sample fluid containing particles of interest, as well as, a sheath source supplying sheath fluid to a nozzle assembly for forming a fluid stream. The nozzle assembly may produce a fluid stream along a flow path with sample and sheath fluid. The nozzle assembly may include a nozzle housing which encloses a nozzle cavity. A sample inlet may be formed in the nozzle housing. An injection tube having a sample outlet can be mounted with the nozzle housing and may extend along the nozzle cavity. The injection tube can have a flow path which provides fluid communication between the sample inlet and the sample outlet. The nozzle housing may further include one or more sheath inlets in fluid communication with the nozzle cavity and a nozzle exit orifice downstream of the sample outlet. The flow cytometer may further include an excitation source for interrogating particles within the fluid stream at an inspection zone and one or more detectors for producing signals representative of emitted or reflected electromagnetic radiation at the inspection zone. An analyzer may be included for analyzing signals produced by the one or more detectors and for making a sort decision. A charge element may charge the fluid stream according to the sort decision for deflection by deflection plates.

Still another embodiment relates to a method of sorting cells which can begin with the step of magnetically coupling a nozzle assembly having a fluid flow path to a flow cytometer. Next a fluid stream may be formed at the nozzle assembly from a sheath fluid and a sample fluid. The fluid stream may be interrogated at an inspection zone which is then perturbed into droplets. Signals representative of emitted or reflected electromagnetic radiation at the inspection zone may then be produced and analyzed for making sort decisions. Finally, droplets may be separated according to the sort decision.

Yet another embodiment provides a nozzle assembly constructed from a nozzle housing which encloses a nozzle cavity. An injection tube having a sample outlet may be disposed within the nozzle cavity and the nozzle cavity may have an elliptical cross section with a major axis at least three times the length of the minor axis at the outlet of the injection tube. One or more sheath inlets may be in fluid communication with the nozzle cavity and a nozzle exit orifice may be located downstream of the sample outlet.

Figure 1:
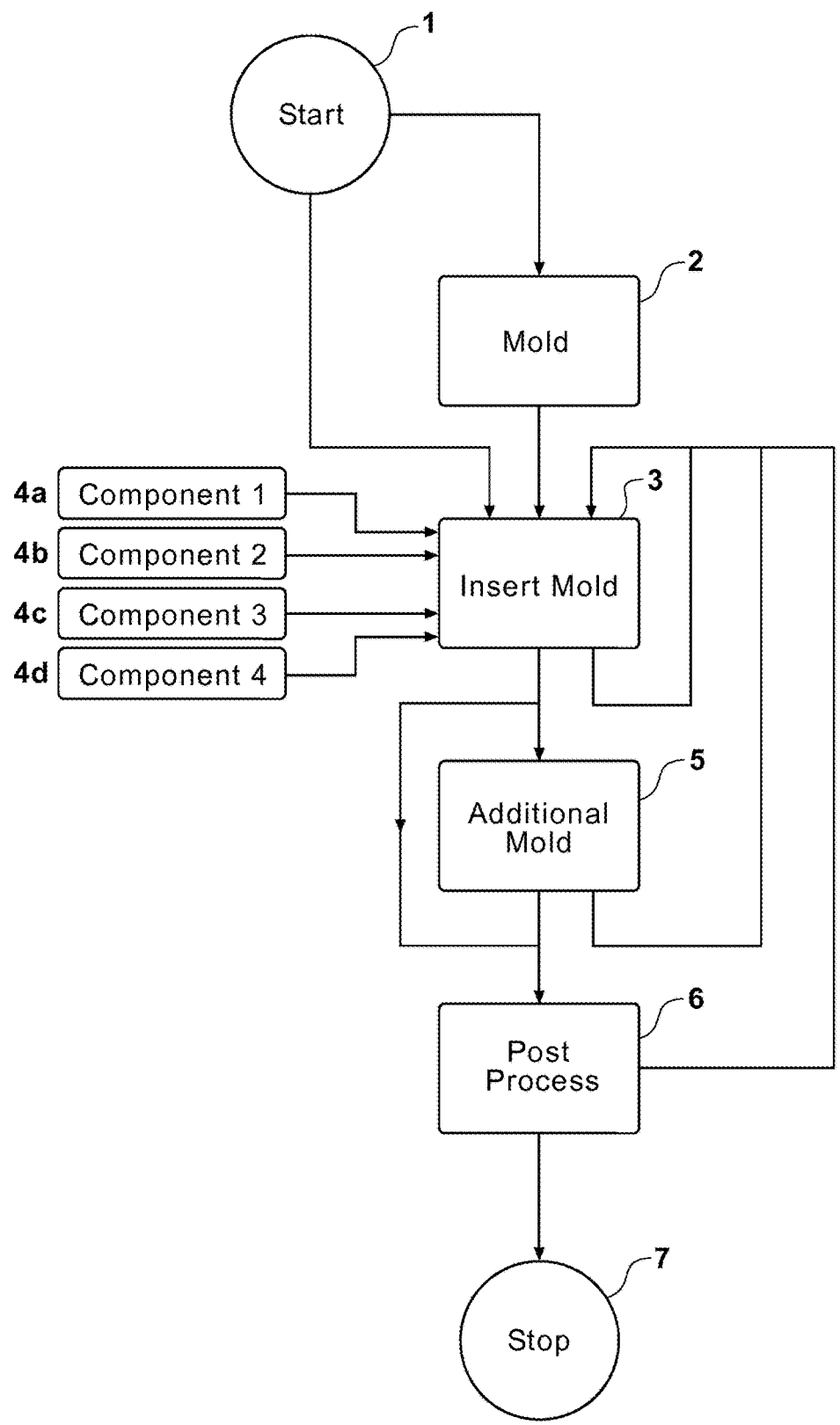
FIG. 1 illustrates a flow chart of a process for producing a nozzle assembly for a flow cytometer.

While the present invention may be embodied with various modifications and alternative forms, specific embodiments are illustrated in the figures and described herein by way of illustrative examples. It should be understood the figures and detailed descriptions are not intended to limit the scope of the invention to the particular form disclosed, but that all modifications, alternatives, and equivalents falling within the spirit and scope of the claims are intended to be covered.

MODE(S) FOR CARRYING OUT THE INVENTION

A flow cytometer may include various individual components assembled into suitable nozzles. The nozzle assemblies are tested to ensure desired performance criteria is met. Such criteria can include whether the nozzle assemblies are providing sufficiently uniform orientation in some applications. Often nozzle assemblies fail to meet the desired performance criteria and are discarded or must be reworked. Occasionally, the position of an injection tube is not provided at precisely the desired length or precisely within a desired radial position, resulting in undesirable nozzle performance. Therefore, a need exists for a method of repeatedly and reproducible manufacturing nozzles having precise performance characteristics.

A certain aspect of the nozzle assembly described herein relates to a straight injection tube which is seated with a portion of the nozzle assembly. By reducing the overall length of the injection tube, it becomes easier to control the length and radial position of the injection outlet. Previous injection tubes often included metallic injection tubes which were bent within the nozzle assembly or which were straightened from coiled, or curved, stock. Whether introduced in a pre-fabrication coiling step or just prior to deployment in a flow cytometer nozzle, such curvatures result in folds or irregularities on the interior of the injection tube and may further create positional uncertainty of the injection tube central axis with respect to the desired flow axis within a nozzle. These folds and irregularities can inhibit laminar fluid flow or can redirect sample flow, which may have a negative impact on the performance characteristics of the nozzle assembly; particularly if orienting characteristics are desired. In another aspect, the over molded injection tube described herein may present a continuous, or flush, surface at any connection point. Various previous nozzle assemblies often included connectors which presented dead volumes in the flow path. These dead volumes can become stagnant pockets of fluid that may harbor bacteria detrimental to the sample and may be difficult to clean. By injection over molding an injection tube into the nozzle assembly a precise, repeatable length and position can be achieved, thereby providing a reliable means of manufacturing nozzle assemblies with precise, reproducible performance characteristics. Additionally, over molding may provide a means for reducing or eliminating dead spaces at various connections. Additional elements may be over molded, or injection molded, with various portions of the nozzle assembly to reduce the number of potential dead spaces as well as the number of connections with the potential for leaking.

Turning to FIG. 1, a flow chart illustrates a process for manufacturing a nozzle assembly for a flow cytometer. The process may begin at the step generally designated "START" 1. Optionally, a portion of the nozzle housing, or a nozzle assembly component, may be molded at the step designated "MOLD" 2. By way of a non-limiting example, one of two pieces forming the nozzle housing may be molded at this step by an injection molding technique, such as by thermoplastic injection molding or by thermoset injection. In the case of thermoplastic injection molding, a mold constructed from two or more cooperating sections forms a cavity having the shape of the nozzle housing piece. Molten resin can be fed into that cavity under pressure and allowed to cool. Other molding techniques, such as transfer molding, compression molding, thermoforming, and other similar techniques may also be used to form portions of the nozzle housing. The molten resin may be selected from polycarbonate, PVC, a plastic, polymer, plastomer, epoxy, phenolic, DAP and thermoplastics such as nylon, acetal, PBT, Polyphenylene oxide, Polyphenylene sulfide, or other similar materials. Although the step is labeled "MOLD," it is also intended to encompass component parts made by fused deposition molding, such as in a 3-D printer (available from Stratasys, Edina, Minn., US).

At the step generally designated "INSERT MOLD" 3 a portion of the nozzle housing may be injection molded, and further may be over molded onto a component of the nozzle assembly. By way of an example, a complimentary piece of the nozzle housing may be formed for coupling with the first piece formed at the MOLD 2 step. Any one of, or any combination of, a first component "component 1" 4a, a second component "component 2", a third component "component 3" 4c, up to an nth component "component n" 4n, may be placed within the mold for over molding with a piece of the nozzle housing. This process may also be referred to as insert molding, by virtue of inserting a nozzle component into the mold. The nozzle components which may be over molded into the nozzle housing may include: an injection tube, an oscillating element, a piezoelectric element, a nozzle tip, a charge pin, an electrical cable, an electrical connector, a nozzle alignment mechanism, a particle alignment mechanism, a sheath inlet connector, a sheath inlet tube, a sample inlet connector, a waste tube, a metallic element, a ceramic element, an optical window, a fastener, and a seating element. Any, or all, of the nozzle components may be molded or manufactured contemporaneously with the steps described, or they may be pre-fabricated or even obtained from off the shelf sources. In one embodiment, an injection tube may be manufactured by a polymer extrusion. Additionally, other components for nozzle assemblies may also be insert molded with a piece of the nozzle housing. In one embodiment, the initial step designated "MOLD" 2 may be skipped entirely and the INSERT MOLD 3 step may comprise molding a single piece nozzle housing. Such an embodiment may include over molding multiple additional nozzle assembly components directly into the single mold. By way of an illustrative example, an injection tube may be precisely aligned and positioned within a mold at the INSERT MOLD 3 step. The mold may be filled with molten resin to precisely, accurately and reproducibly provide the injection tube in a predetermined position in a piece of the nozzle housing. The insert tube may be obtained off the shelf, or may be fabricated, in the MOLD 2 step, and in one embodiment may be constructed from a ceramic, a glass or a polymer. The injection tube may include features for orienting particles, such as an external geometry, an internal geometry, an external bevel, or an internal taper.

The process may include additional iterations of the INSERT MOLD 3 step for insert molding additional nozzle components within additional pieces of the nozzle housing, or for making additional modifications to a piece of the nozzle housing which was previously formed. As one example, the second piece of the nozzle housing may be over molded onto an oscillating element, such as a piezoelectric crystal. This step may undergo any number of iterations and may be repeated any number of times for over molding additional pieces.

After any iteration of the INSERT MOLD 3 step, the process may continue to the step designated "ADDITIONAL MOLD," 5 where additional pieces of the nozzle assembly or pieces of the nozzle housing may be molded. In another embodiment, the ADDITIONAL MOLD 5 step may be skipped. These pieces may be injection molded, transfer molded, compression molded, thermoformed, or formed with other similar techniques. The pieces may be formed from a polycarbonate, PVC, a plastic, or another polymer or plastomer. Additionally, any of these pieces may be produced by fused deposition molding, such as in a 3-D printer.

The process may continue by returning to the INSERT MOLD 3 step, for over molding additional pieces of the nozzle housing with various nozzle components, or the process may continue to the step designated "POST PROCESS" 6. In the POST PROCESS 6 step molded pieces may be finished and connected. The POST PROCESS 6 may include washing, cleaning, sterilizing, curing, machining, and/or coating for any piece produced in the MOLD 2, INSERT MOLD 3, and ADDITIONAL MOLD 5 steps. Additionally, these pieces may be fastened together, or provided with electrical, mechanical or fluid connections at the POST PROCESS 6 step. Following the POST PROCESS 6 step, the method may repeat iterations of the INSERT MOLD 3 or ADDITIONAL MOLD 5 steps. It should be appreciated, that FIG. 1 illustrates a flow diagram, but that one or more of the steps may be carried out independently, or even at the same time.

As one example, a final iteration of the POST PROCESS 6 step may include the steps of incorporating various nozzle components into one of two nozzle housing components, followed by coupling the housing pieces and components into a nozzle assembly. The POST PROCESS step may additionally include various finishing processes, including, but not limited to, glazing, sterilizing, chemical treatments, laser etching, laser detailing, or other post manufacturer processes. This nozzle assembly may be ready to receive fluid and electrical connections for operation in a flow cytometer as designated "STOP" 7. In yet another embodiment, the POST PROCESS 6 may be skipped and the STOP 7 step may be reached after a final iteration of the INSERT MOLD 3 or ADDITIONAL MOLD 5 steps. The final assembly may include a nozzle tip, or the nozzle tip may be supplied later for flow cytometer operation. The process described with respect to FIG. 1 may be incorporated for the manufacture of a large variety of nozzle designs, having a variety of potential elements embedded within the nozzle housing pieces.

Figure 2:
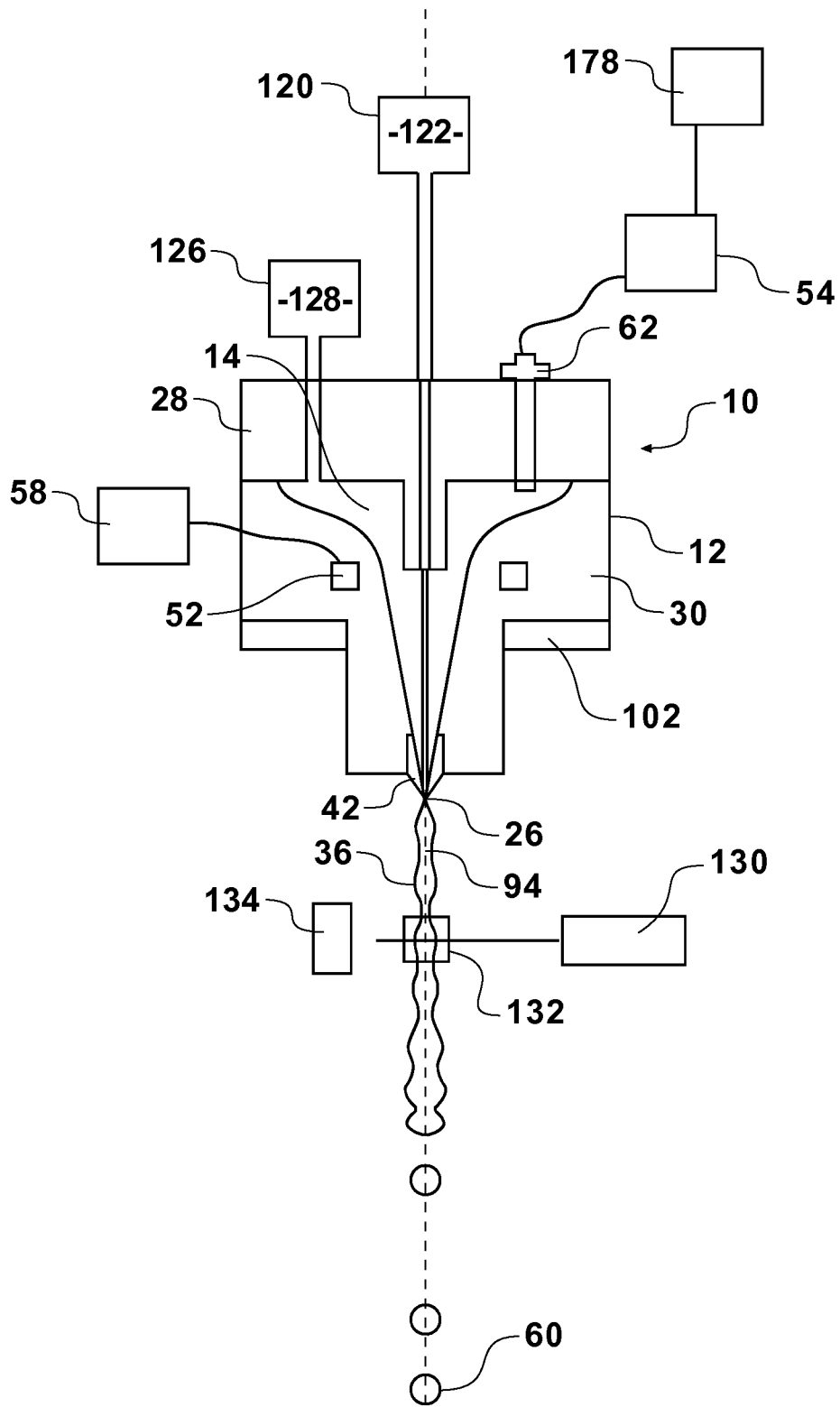
FIG. 2 illustrates a sectional view of a flow cytometer system in accordance with certain embodiments of the present invention.

Turning now to FIG. 2, a flow cytometer system is illustrated which incorporates one example of a nozzle assembly 10 that may be manufactured by the process illustrated FIG. 1. The nozzle assembly 10 may be incorporated at the sort head of any number of commercially available droplet sorters, such as jet-in-air flow cytometers. The nozzle assembly 10 may include a nozzle housing 12 which encloses a nozzle cavity 14. The nozzle housing 12 may be constructed from a single molded housing piece, or may be assembled from a collection of nozzle housing pieces 44, such as two, three, four or more nozzle housing pieces. FIG. 2 illustrates a nozzle housing 10 which includes two nozzle housing pieces 44a, 44b in the form of a nozzle cap 28 secured to a nozzle base 30.

The flow cytometer system may include a sheath source 126 fluidically coupled to the nozzle assembly 10 for proving sheath fluid 128 to the nozzle assembly 10. A sample source 120 may also be coupled to the nozzle assembly 10 for providing sample fluid 122 to the nozzle assembly 10. The sample fluid 122 and sheath fluid 128 may be introduced into a nozzle cavity 14 under pressure and then passed through a nozzle tip 42 having a nozzle exit orifice 26 to form a fluid steam 36 along a flow path having a flow axis 94. The interior of the nozzle assembly 10 may be configured for producing a fluid stream 36 from the nozzle exit orifice 26 in the form of coaxial stream having an inner core stream of sample fluid 122 surrounded by an outer stream of sheath fluid 128.

An oscillating element 52, such as a piezoelectric crystal, may be located within the nozzle assembly 10 for perturbing the fluid stream 36 into droplets 60 some distance below the nozzle exit orifice 26. Previous oscillating elements have been located either above the nozzle cavity or within the nozzle cavity at the top of the cavity. One aspect of the current nozzle assembly 10 relates to an oscillating element 52 which is positioned to surround a portion of the nozzle cavity 14 and reduces the distance between the oscillating element 52 and the nozzle exit orifice 26. The oscillating element 52 may have a ring or toroidal shape with an outer diameter and an inner diameter and may be in communication with a controller 58. The controller 58 may produce a drive signal, such as between about 10 kHz and 120 kHz for perturbing the fluid stream 36 into between about 20,000 droplets per second and 120,000 droplets per second. Frequency and amplitude of the drive signal may be manipulated and/or adjusted by a user through a graphic user interface or through hardware. As but one example, the oscillating element 52 may be located about mid way down the nozzle assembly 10 surrounding the nozzle cavity 14. This location may be within the nozzle housing 12, or external to the nozzle housing 12, but mechanically coupled to the housing. Irrespective of the internal or external location, such an axial placement of the oscillating element 52 is believed to produce droplets more efficiently. In this configuration mechanical vibrations are transferred through nozzle assembly 10 and through the sheath fluid 128 in a speaker like manner to produce a pulsing characteristic in the fluid stream 36. This pulsing characteristic eventually breaks the fluid stream 36 into droplets 60 some distance below the nozzle exit orifice 26. Independent of other inventive features described herein, this application contemplates the benefit of modifying the placement of an oscillating element 52 within or coupled to any nozzle for increased efficiency in producing droplets.

A charge pin 62 may be mounted with the nozzle assembly 10. The charge pin 62 may be constructed from any electrically conductive material and provides an electrical connection between a charging element 52 and sheath fluid 128 contained in the nozzle cavity 14. Through the charge pin 62 a charge may be imparted to the entire fluid stream 36, including a forming droplet just prior to breaking away from the fluid stream 36. An analyzer 178 or other processing device may determine physical or chemical characteristics of particles in the sample and may classify the particles into one or more subpopulations. Based on any instructions relating to the subpopulation in which a particle is classified and other sorting parameters, including a calibrated drop delay, the analyzer 178 will instruct a charge circuit 54 to charge the fluid stream 36 by charging the charge pin 62 just prior to the formation of a droplet in which that particle is expected. In this way, droplets 60 may be supplied with a specific charge, including no charge, based on the characteristics of particles contained within them.

The nozzle assembly 10 may include a nozzle seat 102 for coupling into position on the flow cytometer system. Whereas previous nozzles may have been secured to adjustable stages with fasteners (such as screws, bolts etc.), the nozzle assembly 10 may include a nozzle seat 102 constructed free from fasteners. As one example, the nozzle seat 102 may be coupled to a flow cytometer without the aid of fasteners.

An excitation source 130, such as a source of electromagnetic radiation may be directed to a region know as an inspection zone 132 on the fluid stream 36. Particles within the fluid stream may reflect and/or emit electromagnetic radiation in response to this excitation, and this reflected and emitted electromagnetic radiation may be sensed by one or more detectors 134. These detectors 134 may produce signals representative of the emitted or reflected electromagnetic radiation 136, and those signals may be processed by an analyzer or a detection system to derive a number of chemical and physical properties. The analyzer 178 may then provide instructions to the charge circuit 54 in order to effect the appropriate sort action.

Figure 3:
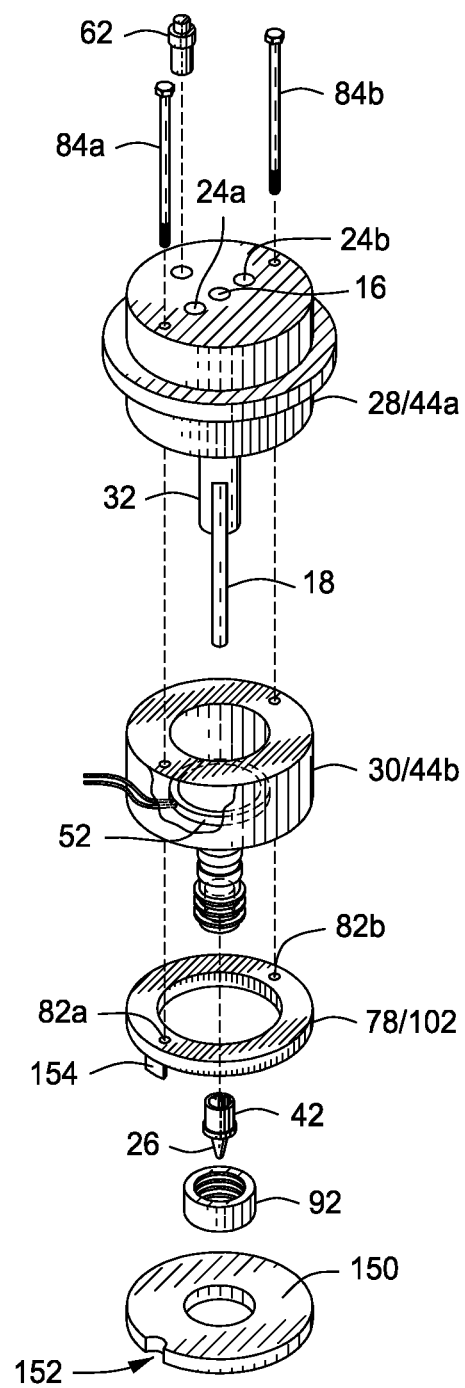
FIG. 3 illustrates an exploded view of a nozzle assembly in accordance with certain embodiments of the present invention.

FIG. 3 illustrates an exploded view of a nozzle assembly 10. Such a nozzle assembly 10 may be produced by a method such as the one described in FIG. 1, or by another process. The exploded view illustrates a first fastener 84*a* and a second fastener 84*b* for securing a first nozzle piece 44*a*, in the form of a nozzle cap 28, and a second nozzle piece 44*b*, in the form of a nozzle base 30, to a nozzle seat 102. The nozzle assembly 10 may, however, be constructed with any number of fasteners 84 and nozzle pieces 44. In the illustrated embodiment, the nozzle seat 102 includes a first threaded portion 82*a* for receiving the first fastener 84*a* and a second threaded portion 82*b* for receiving the second fastener 84*b*. In other embodiments the fasteners may be combined with and/or omitted in favor of adhesives, or other coupling means such as magnets or mechanical means including springs.

The nozzle cap 28 may include a sample inlet 16 which is in fluid communication with an injection stem 32 and an injection tube 18 for forming a fluid flow path. The injection stem 32 may be integrally formed with the nozzle cap 28, or they may be formed as separate nozzle piece. The injection tube 18 may be over molded, or inset molded, with the nozzle cap 28 in a manner which provides fluid communication between the sample inlet 16 and the injection tube 18. This technique can provide for a very short and precisely located injection tube 18. In one embodiment a device may be coupled to the stem 32 which provides a surface with an adjustable axial position. As one example, the injection tube 18 may be over molded onto such an element, which is then mechanically coupled to the injection stem 32. In one embodiment, the injection tube 18 is formed from a smooth rigid material to ensure desired fluid flow properties. In an alternative embodiment, the injection tube is formed from a more pliable material, which may be manipulated after the injection tube is formed or molded. For example, the injection tube may be manipulated to change the initial geometry of a fluid path formed there through for the purpose of encourage a ribbon core stream. As non-limiting example, modifications to the geometry may be incorporated by laser etching certain portions or by a manufacturing step of squeezing the injection tube while in pliable, and not perfectly elastic state. Other manufacturing techniques may also be incorporated to shape the outlet of the injection tube, such that one axis is longer than a second axis. As but an illustrative example, other manufacturing techniques may be employed resulting in an elliptical or rectangular injection tube outlet.

The second nozzle piece 44*b*, in the form of a nozzle base 30, may be dimensioned for coupling with the nozzle cap 28. An oscillating element 52 may be insert molded with the nozzle base 30, or may be potted into a cavity in the nozzle base 30. In one embodiment the nozzle base 30 is dimensioned to receive a nozzle tip 42. For example, the nozzle base 30 may include interior dimensions for coupling with the nozzle tip 42, while the exterior of the nozzle base may be threaded for receiving a retaining nut 92 that holds the nozzle tip 42 in place. In another embodiment, the nozzle tip 42 may be insert molded with nozzle base 30, and in yet another embodiment the nozzle tip may be molded as a portion of the nozzle base 30.

The nozzle seat 102 may take the form of a nozzle clamp 78 which receives the first fastener 84*a* and the second fastener 84*b* in a manner which clamps the nozzle cap 28 to the nozzle base 30. The nozzle seat 102 may be dimensioned for fastener free coupling to the receiver 150. As one example, the nozzle seat 102 can comprise a metallic material coupled to a receiver 150 having magnetic properties. A magnetic material may be located on either one of or both of the nozzle seat 102 and the receiver 150. In a similar embodiment, one or both of these components may be constructed to include electromagnets, or materials which demonstrate magnetic properties in response to electric current. In this configuration, a nozzle assembly 10 may be simply dropped into place and held by gravity and the coupling of magnetic components. Such nozzles are quickly and easily interchangeable. In many environments flow cytometer down time results in lost production time and nozzles seat 102 as described herein provide an extremely efficient method of replacing nozzles and may improve the productivity of a given flow cytometer system. The nozzle seat 102 and receiver 150 may be constructed in a variety of other configuration for coupling the nozzle to a flow cytometer in a fastener free manner. In one embodiment the nozzle seat 102, or the receiver 150, may include springs for securing the two pieces in a fastener free engagement. For example, a spring loaded ball on one component may be designed to lock into socket on the other component. The nozzle seat 102 may also be physically dimensioned for an interlocking configuration with a seat on an adjustable stage at the flow cytometer head. In such an embodiment, the nozzle seat 102 may be so dimensioned for being received by an adjustable stage. Once in place, the nozzle seat 102 may be secured by rotation to achieve an interlocking assembly, or by other mechanical means, such as mechanical means provided on the adjustable stage.

The nozzle seat 102 may include an alignment element 154 in the form of a protrusion which generally extends past a remaining boundary of the bottom surface of the nozzle seat 102. The receiver 150 may include an alignment notch 152. The alignment element 154 and alignment notch 152 may be so dimensioned to favor coupling in specified orientation. In other embodiments, there may be a plurality of alignment notches 152 for potentially securing a single alignment element 154. In this configuration, the nozzle assembly 10 may rest in one of a plurality of predefined orientations relative to the flow cytometer system. In another embodiment, the receiver 150 is adjustable and may be secured in a plurality of positions for modifying the orientation provided by aligning the alignment element 152 and the alignment notch 154. In one embodiment, a spring loaded ball may serve as both a means for engaging the nozzle seat 102 with the receiver 105 and as the alignment element 154 for aligning the two components. While additional components of the flow cytometer have not been illustrated, it should be understood that the receiver 150 may be firmly attached to a stage, such as a stage which is adjustable in two or three dimensions for alignment purposes.

The alignment element 154 and the alignment notch 152, in addition to providing a specified orientation, may provide a precise nozzle location allowing the rapid replacement of a nozzle assembly and minimizing the need for realigning the flow cytometer. In combination with the magnetic coupling, this configuration may eliminate forces which tend to bring the nozzle out of alignment with the detectors or source of electromagnetic radiation. Specifically, torque may be applied to the adjustable stage on which the nozzle sits when fasteners are secured into place by the downward force an operator applies to the fasteners themselves.

Grooves, slots, and other matched surfaces and geometries may also be used, alone, or in combination with magnetic coupling, to provide additional configurations which allow the quick and precise matching to a preferred orientation and/or location. In another embodiment, visual aids in the form of marks or notches may be applied to the nozzle to facilitate the quick and easy replacement of nozzles.

Figure 4:
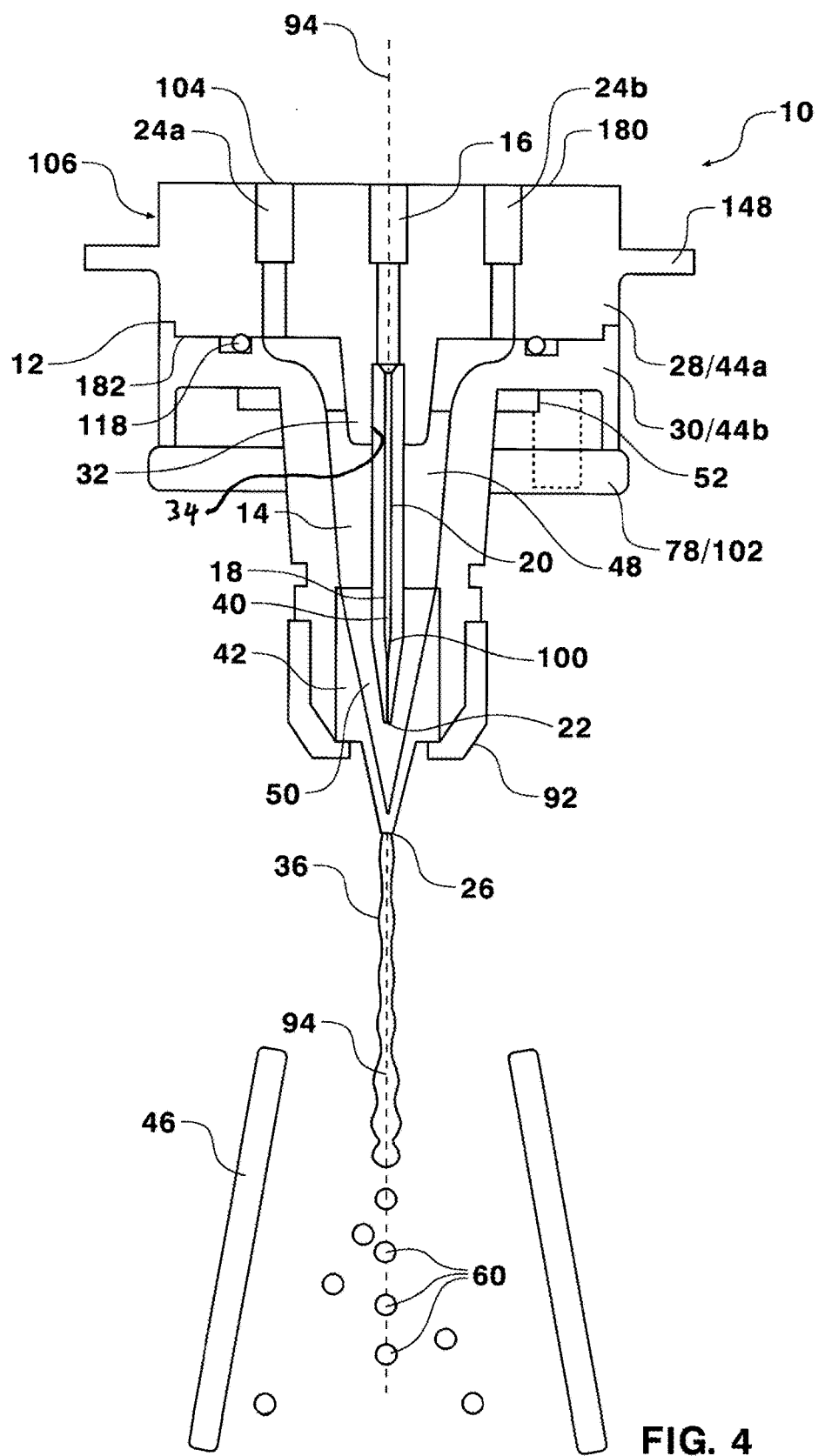
FIG. 4 illustrates a sectional view of a nozzle assembly and other flow cytometer components in accordance with certain embodiments of the present invention.

Turning now to FIG. 4, a more detailed sectional view of a nozzle assembly 10 is illustrated. The view illustrated in FIG. 3 is rotated as compared to FIG. 2. The nozzle housing 12, comprising the nozzle cap 28 and the nozzle base 30, along with the nozzle tip 42 form a nozzle cavity 14. The nozzle cavity 14 comprises an upper cavity 48 and a lower cavity 50. The upper cavity 48 may be considered the portion of the nozzle cavity 14 above the nozzle tip 42, while the lower cavity 50 may be considered the portion of the nozzle cavity 14 formed at the nozzle tip 42. The nozzle cap 28 and the nozzle base 30 may be held in position by nozzle seat 102 in the form of a nozzle clamp 78 which receives fasteners. A sealing element 118 may be provided at the contacting surfaces of the nozzle cap 28 and the nozzle base 30. The sealing element 118 may be an O-ring or another temporary, or permanent sealant. The nozzle tip 42 may be received by the nozzle base 30 and secured into place with a retaining nut 92. The nozzle tip 42 may have a tapering conical cross section, or may have an internal geometry designed to orient aspherical particles. Sperm orienting nozzle tips, like those described in U.S. Pat. Nos. 6,263,745, 7,371,517 and 8,206,988 are contemplated for use with the described nozzle assembly 10 and each patent is incorporated herein by reference in its entirety. The nozzle tip 42 may have a nozzle exit orifice 70 micrometers in diameter and smaller or 60 micrometers in diameter and smaller. In alternative embodiments, the nozzle assembly 10 may be formed from a single injection molded piece or from additional pieces. In an alternative embodiment, the nozzle tip 42, nozzle base 30, and nozzle cap 28 are injection molded to form a single piece nozzle assembly 10. In still another embodiment, the nozzle tip, nozzle base, nozzle cap, and even an injection tube and/or injection stem may be produced as a single piece by a fused deposition molding in a 3D printer. In such an embodiment, the nozzle tip may initially formed without an orifice, which may later be laser etched. Alternatively, a ceramic nozzle tip may be press fit into a nozzle assembly produced in a 3-D printer.

One or more sheath inlets 24a, 24b provide fluid communication from an exterior surface of the nozzle housing 106 to the upper cavity 48 of the nozzle cavity 14. Specifically, the sheath inlets 24 connect a top surface of the nozzle cap 180, which forms a portion of the exterior surface of the nozzle housing 106, to a bottom surface of the nozzle cap 180, which forms a portion of the upper cavity 48. Each sheath inlet 24 may be threaded for receiving a means to attach a sheath line. Alternatively, connectors may be formed integrally with the nozzle cap 28 at each sheath inlet 24. Such integrated connectors may be formed by injection molding the nozzle cap 28 and connectors as single piece. Additionally, a sample inlet 16 may be formed in the top surface of the nozzle cap 180 for communication with the nozzle cavity 14. In one embodiment, tubing maybe directly coupled to the nozzle assembly 10 by over molding or through a secondary manufacturing process, such as by heating, glue or solvents, to provide a flush interior surface and reduce dead volume within the system. Such dead volume may require more cleaning and increases the potential for bacterial build up, leaking, as well as the added expense and labor involved in more frequent replacements.

The sample inlet 16 may continue through an injection stem 32. The injection stem 32 may be formed as a protrusion on the bottom surface of the nozzle cap 180 that extends into the nozzle cavity 14 and includes a pocket 34 for receiving an injection tube 18. A flow path 20 within the injection tube 18 may extend from the sample inlet 16 to a sample outlet 22 disposed within the nozzle cavity 14. Pressurized sample fluid 122 may be introduced through the injection tube 18 into the nozzle cavity 14 and pressurized sheath fluid 128 may be introduced though the sheath inlets 24 a coaxial fluid stream 36 is formed at the sample outlet 22. The fluid steam 36 comprises an inner core stream of sample surrounded by an outer stream of sheath fluid. In certain applications relating to aspherical particles a greater degree of precision may be desirable in the fluid mechanics of the injection tube because fluid mechanics and hydrodynamic forces may be used to attempt to bias the aspherical particles toward a uniform orientation. Independent of other aspects of the disclosed nozzle assembly, an injection tube 18 may be molded from a ceramic, molded or machined from glass, molded or machines from a polymer or other material to provide a smoother exterior surface 70 when compared to injection tubes constructed from metal. Other additive fabrication (versus subtractive ie, milling/machining, turning) techniques may also be used to produce the injection needle 18. Typical metal injection tubes may include irregularities. In the case of bent or curved injections tubes, irregularities such as folds may collect debris effecting flow properties and providing bacteria an opportunity to grow. Another independent improvement in the current nozzle assembly is that the entire length of the injection tube and the entire sample flow path within the nozzle assembly are located in a single flow axis 94 without curves or bends. Such an arrangement may help the predictability of hydrodynamic focusing in orienting nozzles and may help prevent the collection of debris and the associated potential for bacterial infection and clogging or reduced performance.

In one aspect, an injection tube 18 may be formed from a ceramic material which may be molded into varied geometries. The interior surface of a ceramic injection tube can have a varied internal geometry 40. FIG. 4 illustrates the varied internal geometry as an inward taper 100 towards the sample outlet 22 of the injection tube 18. Other varied geometries may be employed depending on the particles to be analyzed or sorted. For example, the interior geometry 40 could be an outward taper, as well as an elliptical or quadrilateral cross section. Other geometries may also be used that are continuous, curved shapes, polygonal shapes, or geometries that contain curved and non-curved shapes. Alternatively, the injection tube 18 may be produced from a polymer extrusion process, which may also result in a particularly smooth interior surface.

The injection tube 18 may be incorporated into the pocket 34 of the nozzle cap 28 by injection over molding to ensure precise alignment injection tube 18 and precise location of the sample outlet. In one embodiment, the injection tube 18 may be precisely seated in the nozzle cap 28 as a short straight tube which is glued into place. Additional components of the nozzle assembly 10 may be over molded or injection molded in order to reduce the number of seals and sealing elements required. When the nozzle cap 28 is mated to the nozzle base 30, the injection tube 18 is provided concentrically within the nozzle cavity 14 with a high degree of precision. As illustrated in FIG. 4 the charge pin 62 may be seen behind the sample inlet.

The nozzle cap 28 may also include a radial extension 148 that may serve as a grip for inserting and removing a fastener free nozzle assembly 10 from a receiver 150. For example, the radial extension may provide a gripping surface for separating the magnetically coupled components.

The oscillating element 52 may be potted in an outer cavity 184 of the nozzle base 30. The oscillating element 52 may be secured by any number of methods and may even be injection molded directly into the nozzle assembly 10, or a portion of the nozzle assembly 10. The outer cavity 184 may be separated from the nozzle cavity 14 by a uniform thickness of material in the nozzle base 30 along the length of the nozzle cavity 14.

Figure 5:
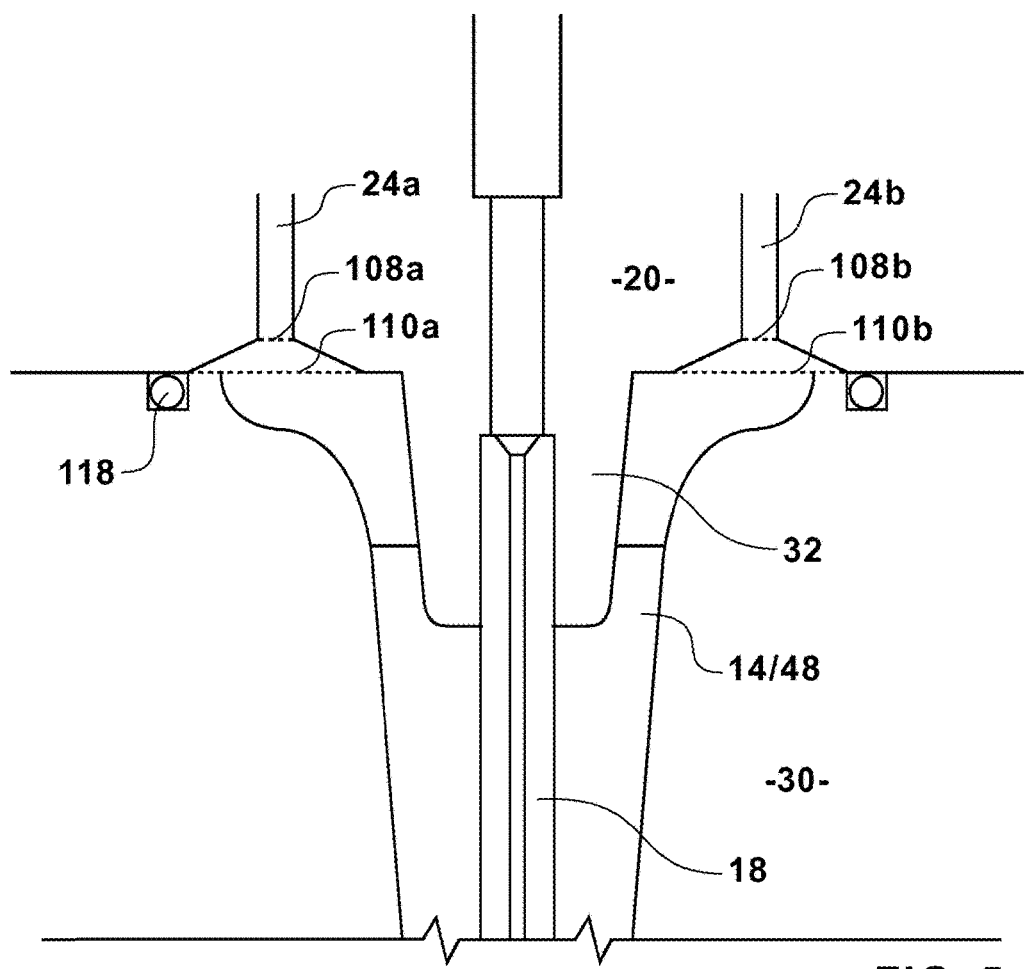
FIG. 5 illustrates a closer sectional view of a portion of a flow cytometer nozzle assembly in accordance with certain embodiments of the present invention.

Turning now to FIG. 5, sheath inlets 24*a*, 24*b* are illustrated in a sectional view of the nozzle assembly 10 at the surface the nozzle base 30 and the nozzle cap 28. The sheath inlets 24*a*, 24*b* may be designed to help prevent bubbles from lingering during or after various rinsing and cleaning cycles. Other surface treatments may be employed to further lessen air bubble entrapment during operation. For example, hydrophobic or hydrophilic treatments, may be applied either during or after nozzle fabrication. Such cycles may include pressurizing the first sheath inlet 24*a* while the second sheath inlet 24*b* remains open to evacuate fluid. Flow may then be reversed by pressurizing the second sheath inlet 24*b* and releasing the first sheath inlet 24*a*. Sheath flow may thus be manipulated in a series of steps for varying durations to clean the interior of the nozzle assembly 10. The turbulence and air introduced in varying the sheath flow during rinsing or cleaning can give rise to bubbles and certain embodiments of the present invention provide for de-bubbling features. A first de-bubbling counter sink 110*a* may be present in the first sheath inlet 24*a* at the nozzle cavity 14. This countersink 110*a* may provide for a first high point 108*a*. Similarly, a second de-bubbling counter sink 110*b* may be present in the second sheath inlet 24*b* at the nozzle cavity 14, providing for a second high point 108*b*. Bubbles that form in the nozzle cavity 14 will tend to rise to the high points 108*a*, 108*b*. Each de-bubbling counter sink 110*a*, 110*b* can extend to the sealing element 118 to capture bubbles on the outer perimeter.

Figure 6:
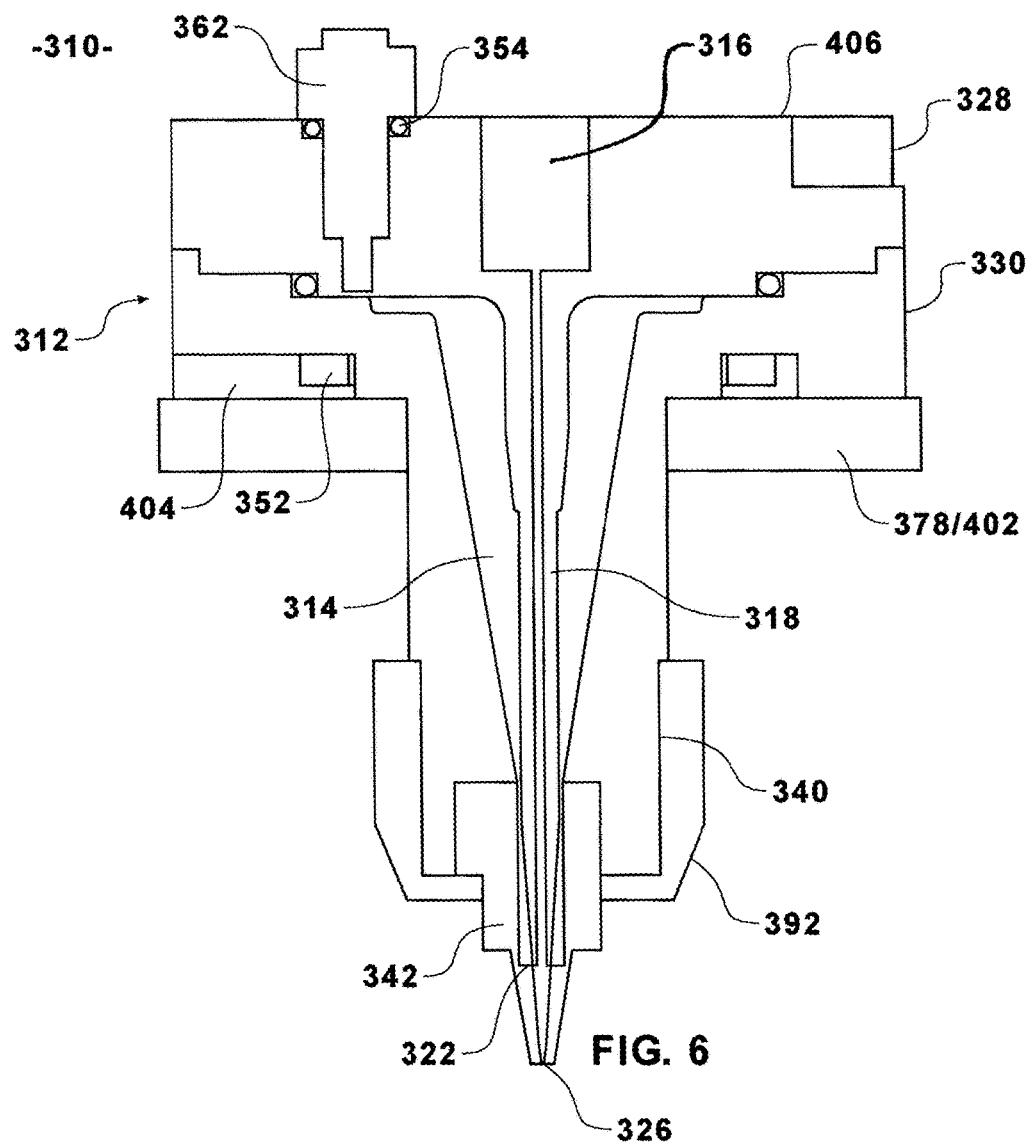
FIG. 6 illustrates a sectional view of a nozzle assembly in accordance with certain embodiments of the present invention.

Turning now to FIG. 6, an embodiment is illustrated which may be constructed through the same process described in FIG. 1. The nozzle assembly 310 may include a nozzle housing 312 constructed from a nozzle cap 328 and a nozzle base 330. The nozzle cap 328 may be constructed with sample inlet 316 at a top surface. The sample inlet 316 may continue along a flow axis and be in fluid communication with a sample outlet 322 of an injection tube 318. The sample inlet 316 may provide fluid communication through an injection tube 318 which terminates at a nozzle tip 342.

The injection tube 318 may influence the flow of a sample fluid, for example with a specified internal geometry 340, while the nozzle cavity 314 geometry may influence the flow of sheath fluid. The sample and sheath are combined at the nozzle tip 342 and exit the nozzle assembly 310 as a co-axial fluid stream. Unlike previous nozzle assemblies, the illustrated nozzle assembly 310 may provide a very aggressive initial taper in its nozzle cavity 314. At the transition between the nozzle cavity 314 and nozzle tip 342, the cross sectional may have an elliptical cross section with a major axis three times longer than the minor axis. This geometry may promote a ribbon core flow, which may help align particles.

Various nozzle components may be incorporated in the nozzle housing 312 through an insert or over molding manufacturing process, or they may be connected to the nozzle assemblies in more conventional manner. For example, the nozzle cap 328 may be over molded onto a charge pin 362. FIG. 5 illustrates a conventional connection, which requires an additional sealing element 354 to prevent leaking and to keep the nozzle cavity operating at a desired pressure.

Similarly, an oscillating element 352 may be potted into an outer cavity 404 of the nozzle base 330. But it also may be over molded with the nozzle base 330, or even located on the exterior of the nozzle base 330. A seating element 402 may also be connected to the nozzle assembly 310. In one embodiment, the seating element comprises a clamp 378 which receives fasteners for securing the nozzle cap 328 to the nozzle base 330. The seating element 402 or clamp 378 may be constructed from a material with magnetic properties, from a magnet, from an electromagnet, or may otherwise be designed for quickly and easily being secured into place on a flow cytometer.

As illustrated in FIG. 5 the nozzle tip 342 is held in place with a retaining nut 392, but the nozzle tip 342 may also be injection molded as a portion of the nozzle housing 312. In a further alternative embodiment, the nozzle tip 342 may be prefabricated and injection over molded with the nozzle base 330.

As can be understood from the foregoing, various nozzle assembly features may be incorporated into a flow cytometer, as well as into a method for manufacturing a flow cytometer. As such, the particular embodiments or elements of the invention disclosed by the description or shown in the figures accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

Moreover, for the purposes of the present invention, the term "a" or "an" entity refers to one or more of that entity;

for example, "a container" refers to one or more of the containers. As such, the terms "a" or "an", "one or more" and "at least one" can be used interchangeably herein.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

We claim:

1. A nozzle assembly comprising:
   a nozzle housing comprising a nozzle cap and a nozzle base that enclose a nozzle cavity, the nozzle housing further comprising an injection stem formed in the nozzle cap that protrudes into the nozzle cavity;
   a sample inlet formed in the nozzle cap of the nozzle housing;
   an injection tube having a sample outlet, the injection tube being mounted with the injection stem and extending along the nozzle cavity, wherein the injection tube comprises a flow path providing fluid communication between the sample inlet formed in the nozzle cap of the nozzle housing and the sample outlet of the injection tube;
   one or more sheath inlets in fluid communication with the nozzle cavity; and
   a nozzle exit orifice downstream of the sample outlet.

2. The nozzle assembly of claim 1, wherein the one or more sheath inlets are formed in the nozzle cap.

3. The nozzle assembly of claim 1, wherein the injection stem further comprises a pocket and wherein the injection tube is mounted with the pocket.

4. The nozzle assembly of claim 1, wherein the nozzle housing is injection molded with the injection tube.

5. The nozzle assembly of claim 1, wherein nozzle housing is over molded onto the injection tube.

6. The nozzle assembly of claim 1, wherein the injection tube comprises a ceramic injection tube.

7. The nozzle assembly of claim 6, wherein the ceramic injection tube is beveled at the sample outlet.

8. The nozzle assembly of claim 6, wherein the flow path is at least partially defined by an interior geometry of the ceramic injection tube.

9. The nozzle assembly of claim 8, wherein the interior geometry of the ceramic injection tube is tapered inwardly towards the sample outlet.

10. The nozzle assembly of claim 8, wherein the internal geometry of the ceramic injection tube at, or towards, the sample outlet is selected from the group consisting of: an oval, a square, a trapezoid, a rectangle, a cone, an inward taper, an outward tape, and combinations thereof.

11. The nozzle assembly of claim 1, further comprising an orienting nozzle tip, wherein the nozzle tip is keyed such that the nozzle tip fits with the nozzle housing in a specified orientation.

12. The nozzle assembly of claim 1, further comprising a seating element mounted with the nozzle housing.

13. The nozzle assembly of claim 12, wherein the seating element comprises a material selected from a group consisting of: a metal, a magnetic material, an electromagnetic material, and combinations thereof.

14. The nozzle assembly of claim 12, wherein the seating element is injection molded with the nozzle housing.

15. The nozzle assembly of claim 12, wherein the seating element comprises a nozzle clamp.

16. The nozzle assembly of claim 15, wherein the nozzle clamp comprises one or more threaded portions for receiving one or more fasteners to secure two or more portions of the nozzle housing.

17. The nozzle assembly of claim 15, wherein the seating element is keyed to ensure the nozzle housing is mounted in a specified position or in a specified orientation.

18. A flow cytometer comprising the nozzle assembly of claim 1.

* * * * *